United States Patent [19]

Wise

[11] Patent Number: 5,219,571
[45] Date of Patent: Jun. 15, 1993

[54] DERMAL FORMULATION FOR GRANULOMA ANNULARE

[76] Inventor: Ronald D. Wise, 9037 Kildare, Skokie, Ill. 60076

[21] Appl. No.: 884,851

[22] Filed: May 13, 1992

Related U.S. Application Data

[63] Continuation of Ser. No. 712,434, Jun. 10, 1991, abandoned.

[51] Int. Cl.$^5$ .................................. A61K 9/10
[52] U.S. Cl. .................................. 424/401; 514/859; 514/949; 514/943
[58] Field of Search .................. 424/401; 514/859, 949

[56] References Cited

U.S. PATENT DOCUMENTS

| | | | |
|---|---|---|---|
| 4,444,570 | 4/1984 | Barth et al. | 424/401 |
| 4,497,794 | 2/1985 | Klein et al. | 514/859 |
| 4,536,399 | 8/1985 | Flynn et al. | 514/859 |
| 4,607,101 | 8/1986 | Bernstein | 514/859 |
| 4,640,932 | 2/1987 | Fong et al. | 514/859 |
| 4,777,034 | 10/1988 | Olivier et al. | 514/949 |
| 4,917,891 | 4/1990 | Kaufmann et al. | 424/401 |

OTHER PUBLICATIONS

Dermatology, S. L. Moschella, M.D. and Harry J. Hurley, M.D. vol. 1, 2nd Edition, 1985 W. B. Saunders, pp. 901–904.
Experimental Granulomatous Inflammation: The Ultrastructure of the Reaction of Guinea Pigs To Bentonite Injection J. Path, vol. 130 (1980) P. J. Browett, L. O. Simpson, J. B. Blennerhassett, pp. 57–64.
Some Methodical and Morphological Aspects of the Bentonite-Induced Inflammatory Reaction in Rat, J. Marel & V. Blaha, 1985 Acta Universitatis Palackianae Olomucensis-Tom. 108 Facultatis Medicae, pp. 151–170.
The Merck Index, Paul G. Stecher, Merck & Co., Inc. 8th Edition, Copyright 1960 p. 126.
Dorland's Illustrated Medical Dictionary, 24th Edition, Copyright 1957, W. B. Saunders Company, p. 191.
Hackh's Chemical Dictionary, McGraw-Hill Book Company, Inc. 3rd Edition, Copyright 1944, p. 105.
Histopathology of the Skin, W. F. Lever, M. D., J. B. Lippincott Company, 5th Edition, p. 204.

*Primary Examiner*—Thurman K. Page
*Assistant Examiner*—Amy Huhna
*Attorney, Agent, or Firm*—Hill, Steadman & Simpson

[57] ABSTRACT

A dermatological formulation or topical preparation containing fine grain bentonite and a lipophilic agent is provided to treat granuloma annulare dermatosis of the skin.

4 Claims, No Drawings

DERMAL FORMULATION FOR GRANULOMA ANNULARE

This is a continuation of application Ser. No. 712,434, filed Jun. 10, 1991, and now abandoned.

FIELD OF THE INVENTION

This invention relates to the art of treating granuloma annulare (an affliction of the skin) to return it to its natural healthy soft textured condition without surgery or pain and especially deals with a bentonite-lipophilic agent, dermatological formulation, or topical preparation to homeopathically reverse the granulomatous process of granuloma annulare without risking infection, scarring or disfigurement.

BACKGROUND OF THE INVENTION

Granuloma annulare (G.A.) is a dermatosis of unknown cause characterized by papules that are usually present in an annular configuration. It has been reported to follow insect bites, sun exposure and trauma. Some cases appear to be due to hereditary predisposition since the lesions have occurred in identical twins and siblings as well as in more than one generation of patients. It is usually idiopathic.

The most common type of G.A. occurs in children and young adults. Lesions are usually asymptomatic, skin-colored, erythematous or violaceous, well defined, dome shaped papules often arranged in a complete or half circle. Solitary lesions may also be present. Lesions are most commonly seen on the dorsa of the hands and feet, but may appear on the forearms, arms, lower legs, and thighs. The face and scalp are rarely affected.

Other types of G.A. include a variant with larger, deep, dermal or subcutaneous nodules which may occur on the palms, legs, buttocks or scalp. The perforating type of G.A. manifests itself as small papules with central umbilication. These lesions are most frequently reported to occur on the hands and fingers. A more rarely encountered variant of G.A. presents as circinate erythematous lesions usually on the trunk. In older adults, the disseminated form of G.A. is more commonly seen. Hundreds to thousands of individual papules arise anywhere on the skin but with usual marked involvement of the trunk.

Patients with G.A. are generally healthy. Recently, the disseminated form of G.A. has been seen more frequently in patients who are serologically HIV positive. Otherwise, laboratory tests are usually normal. The chief laboratory aid in the diagnosis of G.A. is the skin biopsy. Intradermal foci of granulomatous inflammation are detected which have a central core of incomplete, reversible necrosis (necrobiosis) of collagen surrounded by a wall of palisaded histiocytes intermingled with a few acute inflammatory cells. All variants manifest a similar histopathologic finding but the perforating variant also has central lesion ulceration and communication between the area of necrobiosis and the skin surface.

Granulomas are generally formed by the accumulation of monocytes which, upon proper stimulation, develop into macrophages and may further develop into foreign body multinucleated giant cells. The stimulation causing these developments may come from microorganisms, from locally damaged tissue or from foreign material that is introduced into the body. It is known that cutaneous granulomas can result from the contamination of wounds with particles of soil or glass which contain silicon dioxide (silica).

Although the disease has been reported to spontaneously resolve in two years, lesions tend to be recurrent and usually at the originally involved site. Resolution of recurrent lesions have been reported to occur within another three years.

A wide array of treatment modalities has been employed to hasten the resolution of lesions. These include X-ray therapy, cryotherapy, surgical incision and excision, skin grafting, and intralesional injections of corticosteroids. All such treatment methods are invasive and entail risks of secondary infection, scarring and disfigurement. Orally administered salicylates, antimalarials, dapsone and corticosteroids have also been used. These medications are not without potential and dangerous sequelae. Of all these surgical and medical treatments, only the intralesional injection of corticosteroid is said to be of any benefit. However, these injections are painful and may result in disfiguring cutaneous atrophy of the injected areas.

It would therefore be an improvement in this art to provide a bentonite containing dermal formulation or topical preparation for reversing the granulomatous process of granuloma annulare.

Specifically, it would be an improvement in this art to provide a synergistic, small particle size bentonite-lipophilic agent formulation to safely reverse the granulomatous process of granuloma annulare.

SUMMARY OF THE INVENTION

According to this invention, there is provided a dermatological formulation or topical preparation for treating granuloma annulare dermatosis. This formulation or preparation contains small particle sized bentonite, a lipophilic carrier agent, a diluent if needed to control viscosity, and a preservative if needed to prevent microbial growth.

Bentonite is composed of the clay mineral montmorillomite and is a hydrous aluminum silicate. It is an inorganic, non-toxic, non-irritating chemical with the approximate chemical formula $(Al, Fe_{1.67} Mg_{0.33}) Si_4O_{10} (OH)_2(Na^+, Ca^{++}_{0.33})$.

The bentonite can be a commercially available, U.S.P. grade such as the one having the following analysis as expressed in oxides:

| | |
|---|---|
| Silicon dioxide | 67.60% |
| Aluminum oxide | 14.30 |
| Calcium oxide | 1.85 |
| Magnesium oxide | 1.70 |
| Sodium oxide | 1.58 |
| Ferric oxide | 1.08 |
| Potassium oxide | 1.03 |
| Ignition loss | 10.86 |
| | 100.00% |

A useful bentonite also has the following typical properties:

| | |
|---|---|
| Viscosity (5% suspension in water)* | 150 cps |
| Acid Demand | 2.6 |
| Total plate count (aerobic microbes/g) | 100 max |
| Aluminum/Magnesium ratio | 5.0 |
| Moisture | 8.0 (max) |
| Dry particle size (finer than 200 mesh, (74 microns)) | 90% |

| | |
|---|---|
| pH (5% dispersion in water) | 9.0–10.0 |

*Viscosity is very dependent on particle size and size distribution, and can be higher (up to and over 800 centipoise) for other grades of bentonite.

The bentonite is preferably colloidal and preferably has a micron size up to 100 microns although larger sizes of, say, up to 500 microns, may be useful. Large granules of bentonite are not effective and may actually aggravate the granuloma annulare dermatosis.

The carrier portion of the formulation must be a lipophilic agent so that the bentonite will be percutaneously absorbed into the skin.

In general, the lipophilic agent is an agent of low viscosity to be easily spreadable on the skin, preferably odorless, with a melting point of preferably about 3° C. to be spreadable at room temperatures. Any ester of a long chain saturated fatty acid would be acceptable provided it has a low viscosity and is odorless. The carrier must be sufficiently liquid or dilutable enough to make the end product spreadable.

Examples of suitable lipophilic carriers are agents such as:

| | | |
|---|---|---|
| U.S.P. cold cream | Glycerin | |
| Petroleum jelly | Aquaphor ® | }(manufactured by Beirsdorf, Inc. |
| Vegetable oils | Eucerin ® | }P.O. Box 5529, Norwalk, CT 06856-5529) |
| Olive oil | Animal fats such as lanolin | |
| Mineral oil | and anhydrous lanolin | |
| Polyethylene glycols | Hydrocarbons | |
| Propylene glycol | Waxes | |

Viscosity of the product can be controlled by the addition of an alcohol such as ethanol, butanol, propanol, 2-hydroxy propane, and the like.

The preservative material can be any one of a number of non-toxic preservatives such as benzoic acid, methylparaben or the like.

Use of even a preferred amount of bentonite without the lipophilic carrier can create xerosis of the cutis thereby aggravating the granuloma annulare affliction.

It is believed that unobvious synergistic interaction of the fine micron size bentonite and the lipophilic carrier occurs since the bentonite, without this carrier, causes aggravation of the affliction. The bentonite must be percutaneously absorbed and must have a small particle size to create the homeopathical healing.

A general formulation according to my invention includes the following parts by weight:

| | | |
|---|---|---|
| Fine particle size Bentonite | 20–60% | |
| Ester of long chain saturated fatty acid | 20–80% | |
| Alcohol to control viscosity | 0–20% | |
| Preservatives such as methylparaben | 0–0.1% | |
| A preferred formulation in parts by weight is as follows: | | |
| Native hydrated aluminum silicate | 30% | }(particle sizes |
| Native colloidal hydrated aluminum silicate | 20% | }of not more }than about 100 }microns) |
| Tetradecanoic acid, 1-methylethyl ester | 40% | |
| 2-hydroxypropane | 10% | |
| 4-hydroxy benzoic acid, methylethyl ester | 0.1% | |

The above preferred formulation was used to treat six patients having granuloma annulare dermatosis. A dab of the formulation was gently rubbed onto the afflicted areas of the patient's skin daily for 2–6 weeks. After treatment, the lesions were no longer detected in all of the patients.

Bentonite is a native colloidal hydrated aluminum silicate which has high absorbent properties and has been used as an ingestant for the treatment of diarrhea and also used in various cosmetics. It is not a toxic substance and thus safe for such usage. While bentonite has been shown to induce the formation of granulomas when injected into laboratory animals, I have contrary to the teachings of the prior art, developed a successful topical application of bentonite in a lipophilic carrier to reverse the granulomatous process safely via a homeopathic effect.

I have applied my topical preparation on patients having long standing areas with granuloma annulare and have carefully noted the resolution of the lesions at the sites of application.

I believe that the silicate portion of the aluminum silicate (bentonite) molecule mediated the resolution, although the aluminum is possibly also involved in this process. I believe that the active reactant may inhibit an intracellular biochemical reaction of the monocyte that is required for the differentiation of this cell into a macrophage. The reactant may interfere with the recruitment of monocytes into the affected areas or it may inhibit the phagocytic action of the macrophages through some other intracellular or intercellular biochemical interaction. Alternatively, if the collagen has a defect which induces the granuloma formation, the colloidal bentonite particles may coat the affected collagen fibers and mask their putative ability to stimulate the formation of granulomas.

From the above descriptions it will be understood by those skilled in the art that my formulation causes fine grain bentonite to penetrate granuloma annulare affected areas of human skin without any side effects and create a homeopathic reversal of the granulomatosis process permitting the skin to return to a healthy, soft textured condition.

I claim as my invention:

1. The method of homeopathic treatment of granuloma annulare dermatosis which comprises topically administering to the areas of a human patient's skin afflicted by granuloma annulare dermatosis a formulation containing fine grain bentonite having a grain size up to 500 microns dispersed in a spreadable lipophilic agent, rubbing the formulation on the skin to expedite percutaneous absorption of the formulation into the skin to establish a homeopathic reversal of the granuloma annulare affliction, and repeating the topical administration of the formulation as needed.

2. A method of decreasing the lesions of granuloma annulare on a human patient's skin which comprises rubbing into the afflicted areas of the skin a topical formulation comprising 20–60% by weight fine grain colloidal bentonite having a particle size of not more than about 100 microns, 20–80% by weight of an ester of long chain saturated fatty acids, up to 20% by weight alcohol, up to 0.1% by weight of a preservative and with said bentonite uniformly dispersed in said ester and continuing rubbing said formulation into the skin without irritation until it is percutaneously absorbed by the skin.

3. The method of claim 1 wherein the topical administration is carried out at room temperature.

4. A topical preparation for homeopathic treatment of granuloma annulare dermatosis which comprises 20–60% by weight fine grain bentonite composed of about 30% by weight native hydrated aluminum silicate and 20% by weight native colloidal hydrated aluminum silicate, 20–80% by weight of an ester of long chain saturated fatty acids, up to 20% by weight alcohol, up to 0.1% by weight preservative, said bentonite having a particle size of not more than about 100 microns and uniformly dispersed in said ester, said ester comprising tetradecanoic acid, 1 methylethyl ester, and said preparation adapted to be rubbed on the skin of a granuloma annulare infected person to be percutaneously absorbed without irritation.

* * * * *